US005690911A

United States Patent [19]
Mirajkar et al.

[11] Patent Number: 5,690,911
[45] Date of Patent: Nov. 25, 1997

[54] ORAL COMPOSITION CONTAINING A MIXED SURFACTANT SYSTEM FOR PROMOTING ANTIBACTERIAL COMPOUND UPTAKE ON DENTAL TISSUE

[75] Inventors: Yelloji Rao K. Mirajkar, Edison; John Afflitto, Brookside; Nuran Nabi, Cranbury; Abdul Gaffar, Princeton, all of N.J.

[73] Assignee: Colgate Palmolive Company, New York, N.Y.

[21] Appl. No.: 664,225

[22] Filed: Jun. 7, 1996

[51] Int. Cl.[6] ............................................. A61K 7/16
[52] U.S. Cl. .................. 424/49; 424/52; 424/54; 424/55; 424/56
[58] Field of Search ............................ 424/49, 52, 54, 424/55, 56

[56] References Cited

U.S. PATENT DOCUMENTS

| | | | |
|---|---|---|---|
| 4,923,685 | 5/1990 | Wuelknitz | 424/54 |
| 5,188,821 | 2/1993 | Gaffar | 424/52 |
| 5,296,215 | 3/1994 | Burke | 424/49 |
| 5,334,375 | 8/1994 | Nabi | 424/52 |
| 5,470,561 | 11/1995 | Klugkist | 424/49 |

Primary Examiner—Ceila Chang
Attorney, Agent, or Firm—Paul Shapiro

[57] ABSTRACT

An oral composition comprising in an orally acceptable vehicle, an effective antiplaque amount of an halogenated diphenyl ether or phenolic antibacterial compound, and an amount of an mixed anionic/nonionic surfactant system at weight ratios of about 14:1 to 9:1 which ratios are effective to increase the uptake of the antibacterial compound to dental tissue so as to enhance the therapeutic efficacy of the administered antibacterial compound.

24 Claims, No Drawings

ORAL COMPOSITION CONTAINING A MIXED SURFACTANT SYSTEM FOR PROMOTING ANTIBACTERIAL COMPOUND UPTAKE ON DENTAL TISSUE

BACKGROUND OF THE INVENTION

1. Field of the Invention

The present invention relates to an oral composition containing an antibacterial compound for the inhibition of bacterial plaque accumulation on dental tissue and more particularly to an oral composition containing an antibacterial compound and a mixed anionic/nonionic surfactant system which promotes significantly higher uptake of the antibacterial compound on dental tissue.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infections and dental disease associated with plaque formation. For example, halogenated hydroxydiphenyl ether compounds such as triclosan are well known to the art for their antibacterial activity and have been used in oral compositions to counter plaque formation by bacterial accumulation in the oral cavity. The effectiveness of the antibacterial agent is dependent upon its delivery to and uptake by teeth and soft tissue areas of the gums.

There is therefore a need in the art to provide means whereby the delivery to and uptake by dental tissue of antibacterial compounds contained in oral compositions can be promoted so as to enhance the therapeutic efficacy of the antibacterial agent.

SUMMARY OF THE INVENTION

In accordance with this invention there is provided an oral composition comprising in an orally acceptable vehicle, an effective antiplaque amount of an halogenated diphenyl ether or phenolic antibacterial compound, and an amount of a mixed anionic/nonionic surfactant system present at weight ratios effective to increase the delivery and uptake of the antibacterial compound to oral surfaces so as to enhance the therapeutic efficacy of the administered compound.

As will hereinafter be demonstrated, the presence of the mixed surfactant system results in uptake and bioavailability of the antibacterial agent which is unexpectedly higher than for comparable compositions in which the nonionic surfactant is absent from the composition.

DETAILED DESCRIPTION OF THE PREFERRED EMBODIMENTS

The term "oral composition" is used herein to designate products which, in the ordinary course of usage, are retained in the oral cavity for a time sufficient to contact substantially all of the dental surfaces but are not intentionally ingested. Such products include, for example, dentifrices such as toothpaste and gels, mouthwashes, chewing gums and lozenges.

It is essential and critical that the antibacterial containing oral composition of the present invention contain a mixed anionic/nonionic surfactant system wherein the anionic surfactant is the major constituent, the weight ratio of the anionic surfactant to nonionic surfactant being about 14:1 to 9:1 respectively, with the optimum being approximately 9.0:1.0. It is believed that the effectiveness of the mixed surfactants at of this weight ratio is due to the establishment of a mixed micelle system wherein the presence of the indicated amount of a nonionic surfactant reduces the repulsion among head groups in the anionic surfactant micelle thereby increasing the micellar size of the anionic surfactant so that the amount of antibacterial compound solubilized by the anionic surfactant micelle is increased and is available for uptake by dental tissue. However, increasing the nonionic surfactant in the surfactant mixture to an amount resulting in an anionic to nonionic surfactant weight ratio of less than 9:1, e.g., 5:1 produces a dentifrice with unsatisfactory taste characteristics unacceptable to consumers.

The improvement in antibacterial uptake by dental tissue obtained with the applicants present invention is especially surprising in view of the teachings of U.S. Pat. No. 5,470, 561, which is directed to an antiplaque triclosan/zinc salt mouthwash wherein the patentee cites as the critical features of the mouthwash a water level above 60% by weight and an anionic/nonionic surfactant mixture wherein the anionic/nonionic surfactant ratio is 35:4 to 20:5 or 8.75:1 to 4:1. As will hereinafter be demonstrated, an unexpected increase in the uptake of antibacterial compounds on dental tissue from compositions of the present invention is found to occur at water concentrations less than 60% by weight in which the anionic/nonionic surfactant mixture weight ratio is above 8.75:1.

The anionic/nonionic surfactant mixture of the present invention is found to enhance uptake of halogenated diphenyl ether and phenolic antibacterial compounds on dental tissue when incorporated in the oral composition in amounts effective to achieve such enhancement, such amounts being within the range of about 1.0 to about 3% by weight and preferably about 1.25% to about 2%, by weight of the oral composition.

Halogenated diphenyl ether antibacterial compounds useful for the preparation of the oral care compositions of the present invention particularly desirable from considerations of antiplaque effectiveness and safety include 2,4,4'-trichloro-2'-hydroxy-diphenyl ether (triclosan) and 2,2'-dihydroxy-5,5'-dibromo-diphenyl ether.

Phenolic compounds useful in the practice of the present invention include phenol and its homologs, mono and polyalkyl and aromatic halophenols, resorcinol and its derivatives and bisphenolic compounds, such phenolic compounds being more fully disclosed in U.S. Pat. No. 5,368,844, the disclosure of which is incorporated herein by reference. Preferred phenolic compounds are n-hexyl resorcinol and 2,2'-methylene bis (4-chloro-6-bromophenol).

The halogenated diphenyl ether or phenolic antibacterial compound is present in the oral composition of the present invention in an effective antiplaque amount, typically about 0.05% to about 2.0% by weight, and preferably about 0.1% to about 1% by weight of the oral composition.

Anionic surfactants useful in the practice of the present invention include long chain fatty or poly-lower alkoxy groups plus hydrophilic radicals. They will usually be in the form of salts, especially water soluble salts of alkali metals. Useful anionic surfactants include the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl alkali sulfoacetates such as sodium lauryl sulfoacetate; higher fatty acid esters of 1,2-dihydroxypropane sulfonates; the substantially saturated higher aliphatic acyl amides of lower aliphatic aminocarboxylic acid alkali metal salts, such as those having 12 to 16 carbon atoms in the fatty acyl radicals; higher alkyl polylower alkoxy (of 10 to 100 alkoxies) sodium sulfates; higher fatty acid sodium and potassium soaps of coconut oil and tallow, and the like. The anionic surfactant, sodium lauryl sulfate, is preferred in the practice of the present invention.

Nonionic surfactants useful in the practice of the present invention include a nonionic water soluble polyoxyethylene monoester of sorbitol with a $C_{10-18}$ fatty acid ester of sorbitol consisting predominantly of the monoester, condensed with about 20–100, preferably about 20 to about 60, moles of ethylene oxide. The fatty acid (aliphatic hydrocarbon-monocarboxylic acid) may be a saturated or unsaturated acid such as lauric palmitic, stearic, oleic acid. Polyoxyethylene sorbitan fatty esters, sold under the trademark Tween are a preferred class of nonionic surfactants. Tween 20® and Tween 60® are especially preferred, which are a polyoxyethylene (20) and a polyoxyethylene (60) sorbitan monolaurate commercially available from ICI. Another preferred class of nonionic surfactants include polyoxyethylene polyoxypropylene block copolymers having the formula $HO(C_2H_4O)b(C_3H_6O)a(C_2H_4O)bH$ wherein a is an integer such that the hydrophobic base represented by $(C_3H_6)$ has a molecular weight of about 2750 to 4,000, b is an integer such that the hydrophilic moiety represented by $(C_2H_4O)$ constitutes about 70–80% by weight of the copolymer. Block copolymers of this composition are available commercially from BASF under the trademark Pluronic F type.

Pluronic F-77, which has a molecular weight of 6600 and contains 70% of the hydrophilic polyoxyethylene moiety, and Pluronic F-127, which has a molecular weight of 12,600 and contains 70% of the hydrophilic polyoxyethylene moiety, are preferred in the practice of the present invention.

Other nonionic surfactants useful in the preparation of the compositions of the present invention include polyethoxylated glycerol containing six to seven ethoxy groups having a molecular weight of about 400 available under the trademark FINDET from Kao Company, polyethoxylated castor oil available from BASF Company under the trademark Cremaphor and alkyl glucosides produced by reacting glucose or an oligosaccharide with a fatty alcohol containing 12–22 carbon atoms and more preferably with alcohols containing an alkyl group having 12 to 18 carbon atoms. Polyglucosides containing C12–C16 alkyl glucosides are available commercially from Horizon Chemical Division of Henkel, Inc. under the trademark "Plantaren".

In the preparation of an oral composition in accordance with the practice of the present invention, an orally acceptable vehicle including a water-phase with humectant is present. The humectant is preferably glycerine, sorbitol, and/or propylene glycol. Water is present typically in amount of at least about 10% by weight, generally about 30 to 60% by weight and the humectant concentration typically totals about 40–60% by weight of the oral composition.

Dentifrice compositions such as toothpastes and gels also typically contain polishing materials including crystalline silica, having a particle size of up to about 20 microns, such as commercially available Zeodent 115, silica gel or colloidal silica, complex amorphous alkali metal aluminosilicates, hydrated alumina, sodium metaphosphate as well as sodium bicarbonate, calcium carbonate, calcium pyrophosphate, dicalcium phosphate and dicalcium phosphate dihydrate. Typically, the polishing material is included in semi-solid or pasty dentifrice compositions of the present invention in an amount of from about 15 to about 60% by weight and preferably from about 20 to about 55%.

Pyrophosphate salts having antitartar efficacy such as a dialkali or tetraalkali metal phosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphate such as sodium trimetaphosphate may be incorporated in oral compositions of the present invention preferably at concentration of about 0.5 to about 8.0% by weight and preferably about 0.5 to about 3.0% by weight. In liquid oral preparations, the pyrophosphate salts are incorporated at a concentration of about 0.1 to about 2% by weight.

Dentifrices prepared in accordance with the present invention typically contain a natural or synthetic thickener in proportions of about 0.1 to about 5% by weight, preferably about 0.5 to about 2% by weight. Suitable thickeners include Irish moss, i-carrageenan, gum tragacanth, starch, polyvinylpyrrolidone, hydroxyethypropyl cellulose, hydroxybutyl methyl cellulose, hydroxypropyl methylcellulose, hydroxyethyl cellulose, sodium carboxymethyl cellulose and colloidal silica.

The oral composition may also contain a source of fluoride ions, or fluoride-providing compound, as an anticaries agent, in an amount sufficient to supply about 25 ppm to 5,000 ppm of fluoride ions and preferably 500 to 1500 ppm fluoride ions. Among these compounds are inorganic fluoride salts, such as soluble alkali metal salts, for example, sodium fluoride, potassium fluoride, sodium fluorosilicate, ammonium flourosilicate and sodium monofluorphosphate, as well as tin fluorides, such as stannous fluoride and stannous chloride.

An antibacterial enhancing agent may also be included in the oral composition. The use of antibacterial enhancing agents in combination with antibacterial agents such as triclosan is known to the art, as for example U.S. Pat. No. 5,188,821 and U.S. Pat. No. 5,192,531. Preferably, the antibacterial enhancing agent is an anionic polymeric polycarboxylate having a molecular weight of about 1,000 to about 1,000,000, preferably about 30,000 to about 500,000. Anionio polymeric polycarboxylates are generally employed in the form of their free acids or preferably as a partially or fully neutralized water soluble alkali metal salt, e.g., sodium, potassium or ammonium salts. Preferred antibacterial enhancing agents are 1:4 to 4:1 copolymers of maleic anhydride or acid with another polymerizable ethylenically unsaturated monomer, preferably a methyl vinyl ether/maleic anhydride copolymer having a molecular weight (M.W.) of about 30,000 to abut 1,000,000, most preferably about 30,000 to about 500,000. These copolymers are available, for example, under the trademark Gantrez, e.g., Gantrez AN 139 (M.W. 500,000), AN 119 (M.W. 250,000); and preferably Gantrez S-97 Pharmaceutical Grade (M.W. 700,000), of GAF Corporation.

The antibacterial enhancing agent is incorporated in the compositions of the present invention in weight amounts of about 0.05 to about 3%, and preferably about 0.1 to about 2%.

Any suitable flavoring or sweetening material may also be employed in the preparation of the oral compositions of the present invention. Examples of suitable flavoring constituents include flavoring oils, e.g. oil of spearmint, peppermint, wintergreen, clove, sage, eucalyptus, marjoram, cinnamon, lemon, orange, and methyl salicylate. Suitable sweetening agents include sucrose, lactose, maltose, xylitol, sodium cyclamate, aspartyl phenyl alanine methyl ester, saccharine and the like. Suitably, flavor and sweetening agents may each or together comprise from about 0.1% to 5% more of the oral composition.

Various other materials may be incorporated in the oral preparations of this invention such as whitening agents, including urea peroxide, calcium peroxide, and hydrogen peroxide, preservatives, vitamins such as vitamin B6, B12, E and K, silicones, chlorophyll compounds and potassium salts for the treatment of dental hypersensitivity such as potassium nitrate and potassium citrate. These agents, when present, are incorporated in the compositions of the present invention in amounts which do not substantially adversely affect the properties and characteristics desired.

The manufacture of the oral composition of the present invention is accomplished by any of the various standard techniques for producing such compositions. To make a dentifrice, a vehicle is prepared containing glycerol, sorbitol, and propylene glycol, gelling agents and antibacterial agent such as triclosan, and the vehicle and a mixture of anionic and nonionic surfactants are added, followed by blending in of a polishing agent, as well as any polyphosphate and fluoride salts, with the pre-mix. Finally, flavoring agent, is admixed and the pH is adjusted to between 6.8 to 7.0.

The following examples are further illustrative of the present invention, but it is understood that the invention is not limited thereto. All amounts and proportions referred to herein and in the appended claims are by weight, unless otherwise indicated.

EXAMPLE I

The effect of a mixture of anionic and nonionic surfactants when present in an oral composition on the uptake absorption to dental tissue of a halogenated diphenyl ether antibacterial agent was assessed using disks of saliva coated hydroxyapatite (SCHAP), the mineral phase of dental enamel, as an in vitro experimental model for human teeth. The in vitro assessment has been found to be correlatable to in vivo uptake of antibacterial agents on dental tissue surfaces.

In this in vitro assessment, hydroxyapatite (HAP) is washed extensively with distilled water, collected by vacuum filtration, and dried overnight at 37° C. The dried HAP is ground into a powder and 150 milligrams (mgs) of the powder is placed into a chamber of a KBr pellet die (Barnes Analytical, Stanford, Conn.). The HAP powder is compressed for 6 minutes at 10,000 pound in a Carver Laboratory press to prepare 13 mm diameter disks which are sintered for 4 hours at 800° C. in a Thermolyne furnace.

To determine the delivery of triclosan to a SCHAP disk from a dentifrice containing triclosan and an anionic surfactant (sodium lauryl sulphate) mixed in combination with a series of nonionic surfactants, SCHAP disks were treated with a dentifrice slurry prepared from compositions identified in Table I below as Compositions A–G. The amounts of dentifrice slurry used to contact the disks simulated in vivo surface to volume ratios found in the mouth. The dentifrice slurries were a liquid phase solution which contained all the components of a dentifrice except the abrasive. The liquid phase, in part, simulates brushing condition. The weight ratio of the sodium lauryl sulfate to nonionic surfactant used in the Compositions A–G was 9:1. After incubation for 30 minutes at 37° C., the SCHAP disks were removed from the dentifrice slurry, washed three times with water.

The uptake absorption of triclosan, on SCHAP disks, from Compositions A–G is set forth in Table II below.

For purposes of comparison, the procedure of Example 1 was repeated except that no nonionic surfactant was included in the oral composition which was designated "Composition H". The uptake and retention of triclosan from comparative Composition H (the ingredients of which are listed in Table I) is also set forth in Table II below.

TABLE I

| Composition | A | B | C | D | E | F | G | H |
|---|---|---|---|---|---|---|---|---|
| Ingredients: | Wt. % | Wt. % | Wt. % | Wt. % | Wt. % | Wt. % | Wt. % | Wt. % |
| Sorbitol | 20.000 | 20.000 | 20.000 | 20.000 | 20.000 | 20.000 | 20.000 | 20.000 |
| Glycerol | 20.000 | 20.000 | 20.000 | 20.000 | 20.000 | 20.000 | 20.000 | 20.000 |
| Propylene Glycol | 0.500 | 0.500 | 0.500 | 0.500 | 0.500 | 0.500 | 0.500 | 0.500 |
| Sodium Lauryl Sulphate | 1.350 | 1.350 | 1.350 | 1.350 | 1.350 | 1.350 | 1.350 | 1.500 |
| Pluronic 127 | 0.150 | — | — | — | — | — | — | — |
| Pluronic F77 | — | 0.150 | — | — | — | — | — | — |
| Cremaphor GS32 | — | — | 0.150 | — | — | — | — | — |
| Tween 20 | — | — | — | 0.150 | — | — | — | — |
| Tween 60 | — | — | — | — | 0.150 | — | — | — |
| Polyethoxylated Glycerol | — | — | — | — | — | 0150 | — | — |
| Alkyl Polyglucoside | — | — | — | — | — | — | 0.150 | — |
| Triclosan | 0.300 | 0.300 | 0.300 | 0.300 | 0.300 | 0.300 | 0.300 | 0.300 |
| NaF | 0.243 | 0.243 | 0.243 | 0.243 | 0.243 | 0.243 | 0.243 | 0.243 |
| Water | 56.457 | 56.457 | 56.457 | 56.457 | 56.457 | 56.457 | 56.457 | 56.457 |
| Flavor Oil | 1.000 | 1.000 | 1.000 | 1.000 | 1.000 | 1.000 | 1.000 | 1.000 |
| Total | 100.000 | 100.000 | 100.000 | 100.000 | 100.000 | 100.000 | 100.000 | 100.000 |

TABLE II

| Composition | Triclosan Uptake (ppm) | SD* | % Increase Compared to Composition H |
|---|---|---|---|
| A | 67.21 | 16.71 | 36.82 |
| B | 63.39 | 6.18 | 29.05 |
| C | 90.75 | 20.69 | 84.75 |
| D | 67.78 | 10.27 | 37.98 |
| E | 57.08 | 4.38 | 16.21 |
| F | 62.50 | 11.96 | 27.25 |
| G | 65.61 | 13.34 | 33.58 |
| H | 49.12 | 3.94 | — |

*Standard deviation ±

TABLE IV

| Composition | Triclosan Uptake µg/disk | SD* | % Increase as compared to Composition K |
|---|---|---|---|
| J | 59.96 | 1.34 | +35.50 |
| K | 44.25 | 1.91 | — |

*Standard deviation ±

The results recorded in Table IV show that the oral composition containing the SLS/Pluronic F127 surfactant mixture at a 9:1 weight ratio (Composition J) effects a substantial (35.5%) increase in triclosan uptake on SCHAP disks when compared to equivalent amount of SLS (Composition K) used as the sole surfactant.

EXAMPLE III

The procedure of Example I was repeated except the anionic polymeric polycarboxylate Gantrez S-97 was included in oral compositions of the present invention, which compositions were designated Compositions "M–V" wherein these compositions contained SLS and a nonionic surfactant which was either an alkyl glucoside or a polyethoxylated glycerol. For purposes of contrast, an oral composition in which a nonionic surfactant was not included in the composition, designated "Composition W", was also prepared. In compositions M–Q, the dentifrice contained a mixture of anionic (SLS) and nonionic surfactant at a weight ratio of 9:1 and in Compositions R–V the anionic/nonionic surfactant ratio was 14:1. The ingredients of Compositions M–W are listed in Table V below. The triclosan uptake on SCHAP disks of Compositions M–W are summarized in Table VI below.

The results recorded in Table II show that uptake of triclosan on SCHAP disks from Compositions A–G was enhanced by about 16–85% by the presence in the dentifrice of a mixture of anionic (SLS) and nonionic surfactants at a weight ratio of 9:1 (Compositions A–G) as compared to a Composition H in which the anionic surfactant (SLS) was the sole surfactant.

EXAMPLE II

The procedure of Example I was repeated to compare the triclosan uptake on SCHAP disks between a triclosan containing oral composition in which a surfactant mixture of sodium lauryl sulfate (SLS) and Pluronic F127 at a weight ratio of 9:1 was used, designated Composition J and compositions in which SLS was the sole surfactant, designated Compositions K. The ingredients of Compositions J and K are listed in Table III below. The triclosan uptake on SCHAP disks of these compositions is summarized in Table IV below.

TABLE III

| Composition | J | K |
|---|---|---|
| Ingredients | Wt. % | Wt. % |
| Sorbitol | 20.000 | 20.000 |
| Glycerol | 20.000 | 20.000 |
| Propylene Glycol | 0.500 | 0.500 |
| Sodium Lauryl Sulphate | 1.350 | 1.50 |
| Pluronic F127 | 0.15 | — |
| Triclosan | 0.300 | 0.300 |
| NaF | 0.243 | 0.243 |
| Water | 56.457 | 56.457 |
| Flavor Oil | 1.000 | 1.00 |
| Total | 100.000 | 100.00 |

TABLE V

| Composition | M | N | O | P | Q | R | S | T | U | V | W |
|---|---|---|---|---|---|---|---|---|---|---|---|
| Ingredients: | Wt. % | Wt. % | Wt. % | Wt. % | Wt. % | Wt. % | Wt. % | Wt. % | Wt. % | Wt. % | Wt. % |
| Sorbitol | 20.000 | 20.000 | 20.000 | 20.000 | 20.000 | 20.000 | 20.000 | 20.000 | 20.000 | 20.000 | 20.000 |
| Glycerol | 20.000 | 20.000 | 20.000 | 20.000 | 20.000 | 20.000 | 20.000 | 20.000 | 20.000 | 20.000 | 20.000 |
| Propylene Glycol | 0.500 | 0.500 | 0.500 | 0.500 | 0.500 | 0.500 | 0.500 | 0.500 | 0.500 | 0.500 | 0.500 |
| Sodium Lauryl Sulphate | 1.350 | 1.350 | 1.350 | 1.350 | 1.350 | 1.40 | 1.40 | 1.40 | 1.40 | 1.40 | 1.50 |
| Pluronic 127 | 0.150 | — | — | — | — | 0.1 | — | — | — | — | — |
| Pluronic F77 | 0.150 | 0.150 | — | — | — | — | 0.1 | — | — | — | — |
| Cremaphor GS32 | — | — | 0.150 | — | — | — | — | 0.1 | — | — | — |
| Tween 20 | — | — | — | 0.150 | — | — | — | — | 0.1 | — | — |
| Tween 60 | — | — | — | — | 0.150 | — | — | — | — | 0.1 | — |
| Polyethoxylated Glycerol | — | — | — | — | — | — | — | — | — | — | — |
| Alkyl Polyglucoside | — | — | — | — | — | — | 0.150 | — | — | 0.150 | — |
| Gantrez S-97 (12.8%) | 15.625 | 15.625 | 15.625 | 15.625 | 15.625 | 15.625 | 15.625 | 15.625 | 15.625 | 15.625 | 15.625 |
| Triclosan | 0.300 | 0.300 | 0.300 | 0.300 | 0.300 | 0.300 | 0.300 | 0.300 | .0300 | .0300 | .0300 |
| NaF | 0.243 | 0.243 | 0.243 | 0.243 | 0.243 | 0.243 | 0.243 | 0.243 | 0.243 | 0.243 | 0.243 |
| NaOH | 0.6 | 0.6 | 0.6 | 0.6 | 0.6 | 0.6 | 0.6 | 0.6 | 0.6 | 0.6 | 0.6 |
| Water | 40.232 | 40.232 | 40.232 | 40.232 | 40.232 | 40.232 | 40.232 | 40.232 | 40.232 | 40.232 | 40.232 |
| Flavor Oil | 1.000 | 1.000 | 1.000 | 1.000 | 1.000 | 1.000 | 1.000 | 1.000 | 1.000 | 1.000 | 1.000 |
| Total | 100.000 | 100.000 | 100.000 | 100.000 | 100.000 | 100.000 | 100.000 | 100.000 | 100.000 | 100.000 | 100.000 |

TABLE VI

| Composition | Triclosan Uptake (ppm) | *SD | % Increase Compared to Composition W |
|---|---|---|---|
| M | 94.7 | 6.99 | 28.93 |
| N | 89.81 | 1.80 | 22.27 |
| O | 76.96 | 2.37 | 4.78 |
| P | 77.83 | 5.82 | 5.96 |
| Q | 80.18 | 3.82 | 9.16 |

TABLE VI-continued

| Composition | Triclosan Uptake (ppm) | *SD | % Increase Compared to Composition W |
|---|---|---|---|
| R | 91.61 | 1.08 | 24.72 |
| S | 83.61 | 3.37 | 13.83 |
| T | 84.24 | 5.55 | 14.69 |
| U | 89.64 | 9.24 | 22.04 |
| V | 76.39 | 3.48 | 4.01 |
| W | 73.45 | 8.87 | — |

*Standard deviation ±

The results recorded in Table VI show that uptake of triclosan on SCHAP disks from Compositions M–V was enhanced by about 4–29% by the presence in the dentifrice of a mixture of anionic (SLS) and nonionic surfactants at a weight ratio of 9:1 (Compositions M–Q) and at a weight ratio of 14:1 (Compositions R–V) as compared to Composition W in which the anionic surfactant (SLS) was the sole surfactant.

EXAMPLE IV

To determine the antiplaque activity of triclosan containing oral compositions containing a mixed SLS/Pluronic 127 surfactant system of the present invention, oral compositions, designated Compositions "AA" and "BB" containing the ingredients listed in Table VII were prepared. For purposes of comparison, an oral composition which contained only SLS designated Composition "CC", was also prepared, the ingredients of which are also listed in Table VII below.

TABLE VII

| Composition | AA | BB | CC |
|---|---|---|---|
| Ingredients | Wt. % | Wt. % | Wt. % |
| Sorbitol | 20.000 | 20.000 | 20.000 |
| Glycerol | 20.000 | 20.000 | 20.000 |
| Propylene Glycol | 0.500 | 0.500 | 0.500 |
| Sodium Lauryl Sulphate | 1.40 | 1.350 | 1.50 |
| Pluronic F127 | 0.1 | 0.15 | — |
| Triclosan | 0.300 | 0.300 | 0.300 |
| Gantrez S-97 (12.8%) | 15.625 | 15.625 | 15.625 |
| NaF | 0.243 | 0.243 | 0.243 |
| Water | 40.232 | 40.232 | 40.232 |
| Flavor Oil | 1.00 | 1.000 | 1.000 |
| NaOH | 0.6 | 0.6 | 0.6 |
| Total | 100.000 | 100.000 | 100.000 |

The efficacy of Compositions AA–BB, as well as comparative Composition CC, to inhibit bacterial plaque formation in vitro was assessed using the chemostat plaque model as described in Gaffar et al, Am. J. Dent., Vol. 3, Special Issue pages 58–59, (September, 1990). The experimental apparatus includes a chemostat (Bioflo, Model C32), a source of supplementing growth media, a mixing chamber and several flow cells. The flow cells were specifically designed to contain 13 mm×1 mm thick saliva coated hydroxy apatite disks (SCHAP) prepared in accordance with the procedure of Example 1 on which plaque formation was measured.

A mixed culture of five species of oral microorganisms (A. viscosus, S. mutans, S. sanguis, V. parvula, and F. nucleatum) associated with human plaque was maintained in the chemostat, and the culture was then pumped through the flow cells at the rate of 1 ml/minute for 48 hours to grow plaque on the disks. Thereafter the liquid dentifrices were pumped for 30 secs at the rate of 1 ml/minute through the flow cells containing SCHAP disks on which the plaque was grown. A total of four treatments of the SCHAP disks were given at 12 hour intervals during a 48 hour plaque growth period. Thereafter, bacterial plaque grown on the SCHAP disks was removed by immersion of the disks in a 2 ml solution of 0.1N NaOH in a water bath at 37° C. with gentle shaking for 15 minutes. The disks were removed and the NaOH solution was sonicated to disperse the plaque. Turbidity (optical density, O.D.); of the sample was then determined by measuring the absorbance at 610 nm in a spectrophotometer which is turbidity reported as plaque score in Table VIII below Plaque scores indicate the degree of plaque growth on the SCHAP disks, that is the lower the plaque score, the greater the antiplaque activity of the dentifrice slurry being tested.

TABLE VIII

| Composition | SLS/Pluronic F127 Wt. Ratio | Plaque Score | SD* | Plaque Reduction (%) as compared to Composition CC |
|---|---|---|---|---|
| AA | 14:1 | 0.2786 | 0.0906 | 30.99 |
| BB | 9:1 | 0.2388 | 0.0753 | 40.85 |
| CC | — | 0.4037 | 0.0464 | — |

*Standard deviation ±

The plaque scores recorded in Table VIII indicate that the compositions containing the SLS/Pluronic F127 surfactant mixture (Compositions AA, BB) exhibited greater antiplaque activity than a similar composition (Composition CC) in which SLS was the sole surfactant.

EXAMPLE V

To determine the antiplaque activity of triclosan containing oral compositions containing a mixed SLS/Pluronic 127 surfactant system of the present invention, oral compositions, designated Compositions DD–FF containing the ingredients listed in Table IX were prepared. For purposes of comparison, an oral composition which contained only SLS designated Composition "GG" was also prepared, the ingredients of which are also listed in Table IX below.

TABLE IX

| Ingredients | DD Weight % | EE Weight % | FF Weight % | GG Weight % |
|---|---|---|---|---|
| Sorbitol | 20.0 | 20.0 | 20.0 | 20.0 |
| Glycerol | 20.0 | 20.0 | 20.0 | 20.0 |
| Propylene Glycol | 0.5 | 0.5 | 0.5 | 0.5 |
| Sodium Lauryl Sulphate | 1.35 | 1.4 | 1.35 | 1.5 |
| Alkyl Polyglucoside | 0.15 | 0.10 | — | — |
| Polyethoxylated Glycerol | — | — | 0.15 | — |
| Sodium Fluoride | 0.243 | 0.243 | 0.243 | 0.243 |
| Gantrez S97 (12.8%) | 15.625 | 15.625 | 15.625 | 15.625 |
| NaOH (25%)* | 0.6 | 0.6 | 0.6 | 0.6 |
| Triclosan | 0.3 | 0.3 | 0.3 | 0.3 |
| Flavor Oil | 1.0 | 1.0 | 1.0 | 1.0 |
| DD-Water | 40.232 | 40.232 | 40.232 | 40.232 |
| Total | 100.00 | 100.00 | 100.00 | 100.00 |
| SLS/Nonionic Ratio | 9:1 | 14:1 | 9:1 | — |

*pH adjusted to 6.9 ± 0.1

The antiplaque activity of the dentifrice slurries was assessed using the chemostat plaque system of Example IV.

The results of the chemostat study are recorded in Table X below.

TABLE X

| Composition | Plaque Growth | SD* | Plaque Reduction as Compared to Composition GG (%) |
|---|---|---|---|
| DD | 0.0553 | 0.0118 | 55.51 |
| EE | 0.0970 | 0.0621 | 21.96 |
| FF | 0.0853 | 0.0338 | 31.38 |
| GG | 0.1243 | 0.0686 | — |

*Standard deviation ±

The results summarized in Table X show that in the presence of Gantrez S-97, the use of a mixed surfactant system of SLS and either an alkyl glucoside or a polyethoxylated glycerol at a SLS/nonionic surfactant weight ratio of 9:1 reduced in vitro growth on SCHAP disks by about 55% compared to SLS as the sole surfactant while the presence of the polyethoxylated glycerol in the mixed surfactant system reduced plaque growth 31%. The results recorded in Table X further show that small variations in the addition of nonionic surfactant alters the plaque reduction efficacy significantly. All these studies indicate the improved uptake and therefore the increased antiplaque effect due to the use of mixed surfactant system of anionic SLS and a nonionic alkyl polyglucoside or polkyethoxylated glycerol surfactant as compared to anionic SLS surfactant alone.

What is claimed is:

1. An aqueous oral composition exhibiting increased uptake by dental tissue of antibacterial compounds contained therein, the composition comprising in an orally acceptable vehicle containing less than 60% by weight water, an effective therapeutic amount of a halogenated diphenyl ether or phenolic antibacterial compound and a mixture of an anionic and a nonionic surfactants at a weight ratio of about 14:1 to about 9:1.

2. The composition of claim 1 wherein the antibacterial agent is incorporated in the composition at a concentration of about 0.05 to about 2.0% by weight.

3. The composition of claim 1 wherein the antibacterial agent is triclosan.

4. The composition of claim 1 wherein the surfactant mixture is present in the composition at a concentration of about 1.0 to about 3% by weight.

5. The composition of claim 1 wherein the anionic surfactant is sodium lauryl sulfate.

6. The composition of claim 1 wherein the nonionic surfactant is a polyoxyethylene polyoxypropylene block copolymer.

7. The composition of claim 1 wherein the nonionic surfactant is a polyethoxylated castor oil.

8. The composition of claim 1 wherein the nonionic surfactant is a polyoxyethylene sorbital fatty ester.

9. The composition of claim 1 wherein the nonionic surfactant is polyethoxylated glycerol.

10. The composition of claim 1 wherein the nonionic surfactant is an alkyl glucoside.

11. The composition of claim 1 wherein an anionic polymeric polycarboxylate is present in the composition.

12. The composition of claim 11 wherein the anionic polymeric polycarboxylate is a methyl vinyl ether/maleic anhydride copolymer.

13. A method for the treatment and prevention of bacterial plaque accumulation on teeth which comprises preparing an aqueous oral composition comprising an orally acceptable vehicle containing less than 60% by weight water, an effective therapeutic amount of a halogenated diphenyl ether or phenolic antibacterial compound and a mixture of anionic and nonionic surfactants at a weight ratio of about 14:1 to about 9:1, and then administering the composition to the oral cavity, whereby, the antibacterial compound exhibits increased uptake to dental tissue.

14. The method of claim 13 wherein the antibacterial agent is incorporated in the composition at a concentration of about 0.05 to about 2.0% by weight.

15. The method of claim 13 wherein the antibacterial agent is triclosan.

16. The method of claim 13 wherein the surfactant mixture incorporated in the composition at a concentration of about 1.0 to about 3% by weight.

17. The method of claim 13 wherein the anionic surfactant is sodium lauryl sulfate.

18. The method of claim 13 wherein the nonionic surfactant is a polyoxyethylene polyoxypropylene block copolymer.

19. The method of claim 13 wherein the nonionic surfactant is a polyethoxylated castor oil.

20. The method of claim 13 wherein the nonionic surfactant is a polyoxyethylene sorbitol fatty ester.

21. The method of claim 13 wherein the nonionic surfactant is polyethoxylated glycerol.

22. The method of claim 13 wherein the nonionic surfactant is an alkyl polyglucoside.

23. The method of claim 13 wherein an anionic polymeric polycarboxylate is present in the vehicle.

24. The method of claim 23 wherein the anionic polymeric polycarboxylate is a methyl vinyl ether/maleic anhydride copolymer.

* * * * *